US005714007A

United States Patent [19]

Pletcher et al.

[11] Patent Number: 5,714,007

[45] Date of Patent: Feb. 3, 1998

[54] APPARATUS FOR ELECTROSTATICALLY DEPOSITING A MEDICAMENT POWDER UPON PREDEFINED REGIONS OF A SUBSTRATE

[75] Inventors: Timothy Allen Pletcher, Eastampton; Pabitra Datta, Cranbury; Christopher Just Poux, Mercerville, all of N.J.; Randall Eugene McCoy, McConnellsburg, Pa.

[73] Assignee: David Sarnoff Research Center, Inc., Princeton, N.J.

[21] Appl. No.: 471,889

[22] Filed: Jun. 6, 1995

[51] Int. Cl.$^6$ .......... B65B 5/015

[52] U.S. Cl. .......... 118/629; 118/624; 118/634

[58] Field of Search .......... 128/200.14, 200.23; 239/690; 118/621, 629, 634, 624, 631

[56] References Cited

U.S. PATENT DOCUMENTS

| | | | |
|---|---|---|---|
| Re. 30,401 | 9/1980 | White | 204/192 N |
| 3,831,606 | 8/1974 | Damani | 128/266 |
| 3,971,377 | 7/1976 | Demani | 128/266 |
| 4,047,525 | 9/1977 | Kulessa et al. | 128/208 |
| 4,160,257 | 7/1979 | Carrish | 346/159 |
| 4,197,289 | 4/1980 | Sturzenegger et al. | 424/443 |
| 4,538,163 | 8/1985 | Sheridan | 346/15 |
| 4,570,630 | 2/1986 | Elliott et al. | 128/203.15 |
| 4,627,432 | 12/1986 | Newell et al. | 128/203.15 |
| 4,628,227 | 12/1986 | Briere | 315/111.81 |
| 4,664,107 | 5/1987 | Wass | 128/200.23 |
| 4,811,731 | 3/1989 | Newell et al. | 128/203.15 |
| 4,889,114 | 12/1989 | Kladders | 128/203.15 |
| 4,918,468 | 4/1990 | Miekka et al. | 346/159 |
| 4,992,807 | 2/1991 | Thomson | 346/155 |
| 5,014,076 | 5/1991 | Caley, Jr. et al. | 346/159 |
| 5,027,136 | 6/1991 | Fotland et al. | 346/159 |
| 5,031,610 | 7/1991 | Armstrong et al. | 128/200.23 |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,186,164 | 2/1993 | Raghuprasad | 128/200.14 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 128/203.15 |
| 5,278,588 | 1/1994 | Kubelik | 346/259 |
| 5,301,666 | 4/1994 | Lerk et la. | 128/203.15 |
| 5,327,883 | 7/1994 | Williams et al. | 128/203.12 |
| 5,328,539 | 7/1994 | Sato | 156/275.5 |

FOREIGN PATENT DOCUMENTS

| | | |
|---|---|---|
| WO 93/0983 | 5/1993 | WIPO . |
| WO 94/08552 | 4/1994 | WIPO . |
| WO 94/13271 | 6/1994 | WIPO . |
| WO 94/23772 | 10/1994 | WIPO . |
| WO 95/00127 | 1/1995 | WIPO . |

*Primary Examiner*—Donald E. Czaja
*Assistant Examiner*—Calvin Padgett
*Attorney, Agent, or Firm*—William J. Burke

[57] ABSTRACT

Apparatus and a concomitant method for electrostatically depositing select doses of medicament powder at select locations on a substrate. Specifically, the apparatus contains charged particle emitter for generating charged particles that charge a predefined region of a substrate and a charge accumulation control circuit for computing the amount of charge accumulated upon the substrate and deactivating the emitter when a selected quantity of charge has accumulated. Additionally, a triboelectric charging apparatus charges the medicament powder and forms a charged medicament cloud proximate the charged region of the substrate. The medicament particles within the medicament cloud electrostatically adhere to the charged region. The quantity of charge accumulated on the substrate at the predefined region and the charge-to-mass ratio of the medicament powder in the cloud control the amount (dose) of medicament deposited and retained by the substrate. Consequently, this apparatus accurately controls both medicament dosage and deposition location. Furthermore, since the substrate can be of any dielectric material that retains an electrostatic charge, the apparatus can be used to deposit medicament on substrates that are presently used in oral medicament consumption, e.g., substrates that are used to fabricate suppositories, inhalants, tablets, capsules and the like.

34 Claims, 4 Drawing Sheets

APPARATUS FOR ELECTROSTATICALLY DEPOSITING A MEDICAMENT POWDER UPON PREDEFINED REGIONS OF A SUBSTRATE

The invention relates to dry powder deposition techniques and more particularly, the invention relates to a technique for electrostatically depositing a dry powder medicament in accurate, repeatable doses upon a dielectric substrate.

BACKGROUND OF THE DISCLOSURE

Powdered medication is typically administered orally to a person as a tablet or capsule, or as an inhalant. The prior art discloses a number of techniques for administering doses of inhalable dry powders to the lungs of a patient. Generally, inhalers are mechanical systems that generate a metered cloud of medicament powder for inhalation by a patient. Many of these prior art inhaler devices use chlorofluorocarbon (CFC) gas to facilitate generating a metered cloud of medicament for inhalation. However, since CFCs are no longer used in consumer products, other techniques for generating the medicament cloud have been explored.

One example of a non-CFC, prior art inhaler is disclosed in U.S. Pat. No. 4,811,731 issued Mar. 14, 1989 (the "'731 patent"). This patent discloses an inhaler that contains a plurality of measured doses of medicament stored in a blisterpack. Upon use, one of the Misters in the blisterpack is punctured and a patient inhales the medicament from the punctured blister via a mouthpiece of the inhaler. In the '731 patent, the medicament dosage is measured and deposited in each blister of the blisterpack using conventional, mechanical measuring and depositing techniques. Detrimentally, such mechanical deposition techniques do not apply repeatable doses of medication into each blister of the blisterpack. Typically, some of the medicament adheres to the mechanical deposition system and, as such, reduces the amount of medication deposited into a given blister. The degree of adhesion depends upon the environment in which the deposition is conducted, e.g., the ambient humidity, temperature and the like. Since a mechanical deposition process is used to apply medicament to other orally administerable platforms, the same dose variation evident in inhaler doses occurs for other platforms as well. As such, a more accurate technique is needed in the art for depositing medication into any orally administerable platform including inhalers, tablets, capsules, suppositories, and the like.

An example of a technique for producing orally administered medication in tablet or capsule form is disclosed in U.S. Pat. No. 4,197,289 issued Apr. 8, 1980. This technique utilizes an electrostatic deposition process for depositing a medicament upon an edible substrate that is referred to in the '289 patent as a "web". Using a conventional corona charging technique, this process continuously charges the web as the web moves past the charging element. Thereafter, the web passes though a compartment containing a medicament cloud. The medicament in the cloud is attracted to the charged web and becomes deposited thereupon, i.e., the web becomes "loaded". A spectroscopic monitoring system determines the amount of medication that has been deposited on the web and generates a control signal that regulates the amount of medicament within the cloud chamber. As such, the '289 deposition technique uses an active feedback system to regulate the deposition process. To complete the process, the loaded web is cut into individual units that can be combined with one another to define a medicament dose, e.g., a particular number of individual web units defines a single dose of the medication. The combined units are then encapsulated to form individual, orally administerable doses of medication.

A disadvantage of the '289 technique is the requirement for an active feedback system to control the deposition process. Such systems are typically complex and require an integrated medicament measuring system to generate the control signals, e.g., such as the spectroscopic monitoring system of the '289 patent. In using a feedback system, the '289 technique attempts to uniformly deposit the medicament across the entire web. Dosage control is therefore accomplished not by changing the deposition quantity upon the web, but rather by combining a number of web units to form a dose. As such, the dosage control process is unduly complicated. For example, to generate a uniform deposit of medicament, the electrostatic charge on the web must be uniform, the rate at which the web passes the charging element and the cloud compartment must be constant, and the feedback system must accurately measure the amount of drug on the web and accurately control the amount of medication in the cloud compartment. Thereafter, assuming the medication was uniformly deposited on the web, the web must be accurately cut into units that can be combined and encapsulated to form doses of the medication. Each of the encapsulated doses is supposed to contain the same amount of medication as all other doses. However, such a complicated process is prone to error.

Therefore, a need exists in the art for a medicament deposition process that electrostatically deposits specific quantities of dry powder medication at particular locations on a dielectric substrate. Additionally, a need exists in the art for a technique for quantifying an amount of electrostatic charge accumulated on the substrate and to use the quantified charge value to regulate the quantity of medicament deposited on the substrate.

SUMMARY OF THE INVENTION

The disadvantages heretofore associated with the prior art are overcome by an inventive technique for electrostatically depositing dry powdered medication at specific locations upon a dielectric substrate. Specifically, a conventional ionographic print head is utilized to charge a particular region of a substrate. The substrate is a planar, dielectric layer positioned upon a conductive plate. To form a dielectric layer that is in contact with the conductive plate, the dielectric layer may be deposited upon the plate, the dielectric layer may be in contact with but independent from the plate, or the plate may be metallic plating deposited upon a lower surface of the dielectric layer.

In operation, a potential is applied between the plate and the print head such that the plate attracts ions generated by the print head. Consequently, the ions electrostatically charge a region of the dielectric layer that lies between the plate and the print head. Selectively positioning the print head relative to the substrate selects particular regions of the substrate upon which to "print" the charge. The amount of charge accumulated at any one location depends upon the dwell time of the print head over that particular location and the ion current between the print head and the plate.

Once a charge is accumulated on the substrate, a triboelectric charging process produces a charged cloud of medicament proximate the charged region of the substrate.. The triboelectric charging process mixes, in a glass container, the dry powder medicament with a plurality of glass or plastic beads. The mixing action charges the medicament. A gas is then used to blow the charged medicament from the container and into a cloud proximate the charged surface of the substrate. The medicament particles are typically oppositely charged with respect to the charge on the substrate. As such, the medicament deposits itself upon the charged region of the substrate. The deposition pattern of the medicament matches a charge pattern "printed" by the print head and the amount of medicament that adheres to the patterned region is proportional to the amount of charge accumulated by the substrate. Consequently, using the invention, the medicament can be accurately positioned on a substrate and the dose can be accurately controlled by controlling the amount of charge accumulated on the substrate.

In one embodiment of the invention, the print head is combined with charge measuring apparatus for quantifying the charge accumulated on the substrate. The measuring apparatus measures the DC current (ion current) between the print head and the conductive plate. Specifically, the plate is connected to an integrator that charges a capacitor as the ions bombard the substrate. A comparator compares the integrator output signal to a threshold level. The threshold level represents of a specific mount of charge to be accumulated on the substrate. When the integrator output signal exceeds the threshold level, the comparator deactivates an AC signal source that generates the ions within the print head. As such, the print head stops generating ions and charge no longer accumulates on the substrate. Consequently, a specific amount of charge has been applied to the substrate and, when the medicament cloud is applied to the charged surface, a particular amount of medicament adheres to the substrate. In this manner, the charge control process very accurately controls the quantity of medicament that is retained by the substrate.

In a further embodiment of the invention, a reverse development process is used to electrostatically deposit medicament powder on a substrate. In a reverse development process, a charge is deposited over the entire substrate surface, except in regions where the medicament is to be deposited. To pattern the charge and generate uncharged regions, either the print head is selectively modulated (activated and deactivated) as it is moved over the surface of the substrate or a photoconductive substrate is used such that, after charging, light is used to selectively remove charge from particular regions of the substrate. In either instance, if, for example, a negative charge is applied to the substrate, a negative charge is also applied to the medicament. As such, the medicament adheres to the substrate in the uncharged regions only, i.e., an electrostatic force is produced between the conductive plate and the medicament in the uncharged regions.

The types of substrates upon which the medicament can be deposited vary widely depending upon the ultimate application of the medication. For example, in an inhaler application, the substrate can be a flat, ceramic disk upon which a plurality of medicament doses are positioned. A user may selectively remove and inhale each dose of the medicament from the disk using a venturi effect inhaler device. Alternatively, the disk may be a fabricated of a woven or perforated dielectric material. In this case, a user can directly position a delivery tube within the inhaler device over a selected dose of medicament stored on the disk. The user then inhales air through the delivery tube and the air flow releases the medicament from the dielectric. The released medicament continues through the delivery tube into the user's lungs.

In a further example of the invention being used to produce oral medication, including capsules, tablets, vaginal and rectal suppositories and the like, the electrostatic deposition technique of the invention is used to electrostatically deposit specific quantities of powdered medicament upon an edible or otherwise biodegradable substrate. The substrate is then encapsulated in an inert material to form a capsule, tablet, or suppository. Substrates useful for this application are typically polymeric substances that preferably self-destruct or degrade in body fluids and/or enzymes. However, the substrate can be an indestructible substance that is readily eliminated from the body once the medicament has been released from the substrate into the body.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present invention is apparatus and a concomitant method for electrostatically depositing a specific quantity of dry powder medicament at select locations on a substrate. The apparatus contains an ionographic print head, an AC signal supply for generating ions within the print head, a DC signal source for propelling the ions toward a substrate, and a charge accumulation control circuit for computing the amount of charge accumulated upon the substrate and deactivating the AC signal source when a specific quantity of charge has accumulated. Additionally, a triboelectric charging apparatus is used to charge the medicament powder and form a charged medicament cloud proximate a predefined region of the substrate that is charged by the print head. The medicament particles within the medicament cloud electrostatically adhere to the predefined region. The quantity of charge accumulated on the substrate at the predefined region and the charge-to-mass ratio of the medicament powder in the cloud controls the amount (dose) of medicament that is deposited upon and retained by the substrate. Consequently, this apparatus accurately controls both medicament dosage and deposition location. Furthermore, since the substrate can be fabricated of any dielectric material that will retain an electrostatic charge, the apparatus can be used to deposit medicament on many substrates that are presently used in oral medicament consumption, e.g., substrate materials used to fabricate suppositories, inhalants, tablets, capsules and the like.

Figure 1:
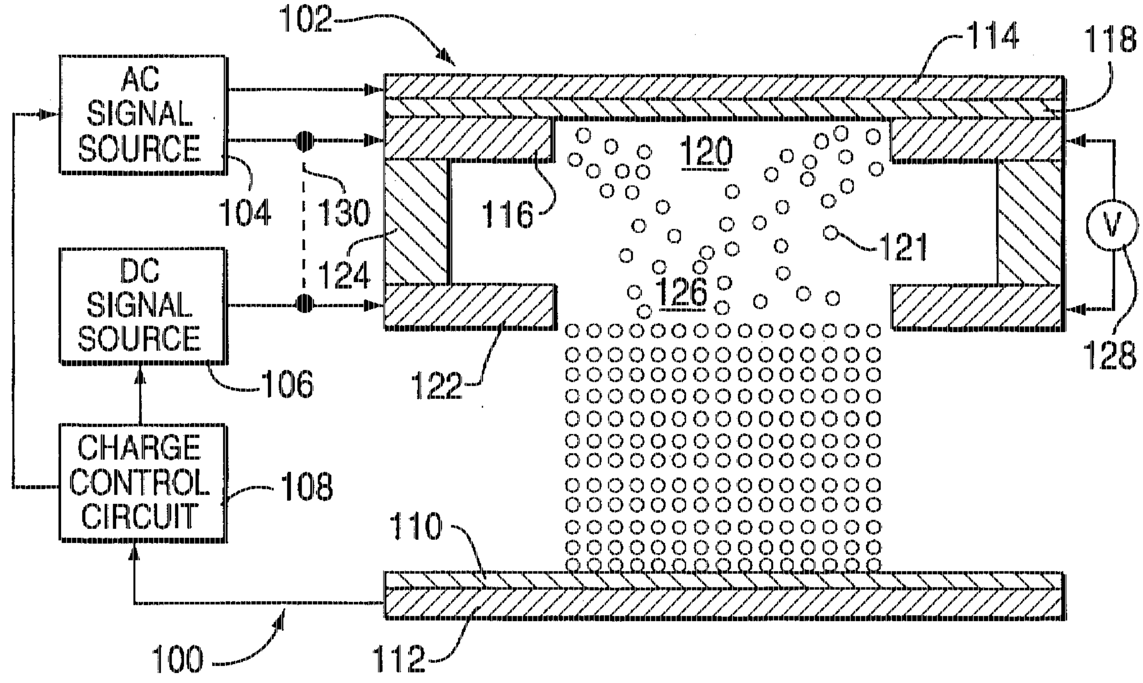
FIG. 1 depicts a cross-sectional view of an ionographic print head and a dielectric substrate supported by a conductive plate.

Specifically, FIG. 1 depicts apparatus for depositing a predefined quantity of charge at a particular location on a dielectric substrate 110. Specifically, the apparatus 100 is comprised of an ion emitter commonly referred to as an ionographic print head 102, AC and DC signal sources 104 and 106 for the print head, a charge control circuit 108 and a dielectric layer 110 (substrate) supported by a conductive plate 112. More specifically, the print head 102 contains a first electrode 114 separated from a second electrode 116 by an insulator 118. The AC signal source 104 typically supplies a 5 MHz RF signal of approximately 1500 peak-to-peak volts across the first and second electrodes. The second electrode contains an aperture that forms an ion generation region 120. The AC signal causes an electric field between the electrodes to form a plasma in region 120. Specifically, the air within this region becomes ionized forming the plasma. To remove the ions 121 from the region and propel them towards the substrate, a screen grid 122 is positioned in a spaced-apart parallel relation to the second electrode 116 and the grid 122 contains an aperture 126 that is coaxially aligned with the region 120. Insulating layer 124, located between the screen grid 122 and the second electrode 116, maintains the screen grid 122 in this spaced-apart relation with respect to the second electrode 116.

Typically, to control ion extraction from region 120, a DC voltage source 128 is connected between the screen grid and the second electrode. However, empirical study indicates that a voltage of zero volts applied between the second electrode and the screen grid permits effective extraction of ions from region 120. As such, the second electrode can be electrically connected to the screen grid as indicated by dashed line 130. However, the optimum screen grid to second electrode voltage may vary depending upon the screen grid bias voltage, the AC voltage and frequency, and the particular structure of the ion emitter. Thus, for best results, a variable DC voltage source 128 should be used to optimize ion extraction.

A bias voltage from a DC signal source 106 is applied to the conductive plate 112 and the screen grid 122. The source 106 supplies a bias voltage of approximately 1200 volts that propels the ions through the screen grid aperture 126 toward the substrate 110. Additionally, acceptable charge deposition has resulted from bias voltages in the range of 400 to 600 volts. The ions form a path that generally follows the electric field lines of force spanning between the screen grid and the plate. The gap between the grid and the substrate is approximately 20 mils. Also, the screen grid, by having this bias voltage applied thereto, selects the polarity of ion that is propelled to the substrate, e.g., a negative biased screen grid propels positive ions toward the substrate, while a positive bias propels negative ions toward the substrate. Typically, the screen grid is negatively biased and the conductive plate is maintained at a ground (0 volt) potential. In this manner, the screen grid assists in the propulsion of the negative ions to negatively charge the substrate at a location on the substrate that is directly below the print head.

The ion current that flows from the screen grid 122 to the plate 112, during any given unit of time, and returns through DC source 106 is equal to the amount of charge accumulated on the substrate. As such, to measure the charge accumulation and control the amount of charge accumulated on the substrate, a charge control circuit 108 is connected in series with the DC signal source. The charge control circuit (which is discussed in detail below with respect to FIG. 2) measures the current flowing between the plate 112 and the screen grid 122. When the current attains a predefined level, the charge control circuit deactivates the AC signal source and, consequently, halts the flow of ions to the substrate. In essence, the charge control circuit modulates the AC signal from the AC signal source. Upon cessation of the ion flow, no further charge accumulation occurs on the surface of the substrate. Thus, the substrate attains and maintains a predefined charge quantity at a particular location on the substrate.

In the foregoing discussion, the print head was discussed as being an ion emitter having two electrodes and a screen grid. Such emitters are commercially available as model 1013527 manufactured by Delphax, Inc. located in Toronto, Canada. It should be understood that this particular emitter arrangement is meant to be illustrative and that other electrode and grid arrangements are available in the art that would produce the necessary localized charge accumulation on the surface of the substrate. Furthermore, the emitter can also be an electron beam emitter that propels a stream of electrons toward the substrate to locally charge the surface of the substrate. As such, the invention described herein encompasses all possible forms of charged particle emitter that can conceivably charge the surface of a dielectric substrate in a localized manner.

Although an "off-the-shelf" ion emitter will sufficiently charge the substrate, empirical study indicates that superior charge deposition is achieved when using a smaller screen grid aperture 126 than is generally available in an off-the-shelf emitter. As such, to reduce the size of the charge accumulation area when using the model 1013527 Delphax emitter, the standard emitter is fitted with a conductive plate (a retrofit screen grid) that reduces the typical 6 mil diameter screen grid aperture to a 1–2 mil diameter aperture. In other words, the retrofit screen grid having a 1–2 mil diameter aperture is coaxially aligned with the standard screen grid aperture to form a composite screen grid with a 1–2 mil diameter aperture. The screen grid bias voltage is applied to the retrofit screen grid. Of course, rather than using a retrofit screen grid, the emitter could merely be fabricated with a 1–2 mil screen grid aperture.

Figure 2:
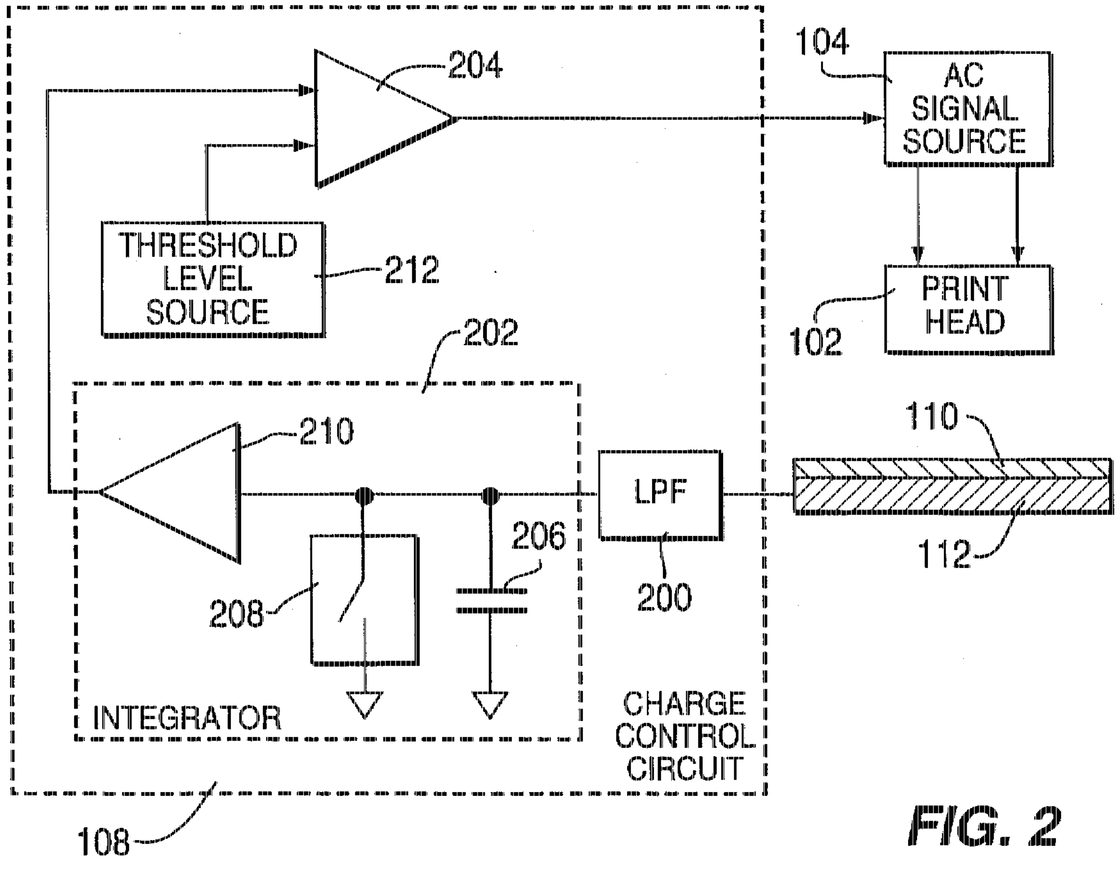
FIG. 2 depict a schematic drawing of a charge accumulation control circuit for use in conjunction with the print head of FIG. 1.

FIG. 2 depicts a schematic diagram of the charge control circuit 108. The circuit contains a low pass filter (LPF) 200, an integrator 202, a comparator 204 and a threshold level source 212. The integrator further contains a capacitor 206, a capacitor discharge component such as a mechanical, electro-mechanical, or solid state switch 208, and a high impedance amplifier 210. Specifically, an input port of the filter 200 is connected to the conductive plate 112 that supports the dielectric substrate 110. The filter removes any RF energy (e.g., AC signal from the AC signal source) that is coupled from the emitter 102 to the plate 112, leaving only the DC signal that represents the ion current. The output port of the filter is coupled to the capacitor 206. The capacitor is connected between the output port and ground. As such, the capacitor charges to a voltage that represents the magnitude of the DC signal produced by the filter 200. The capacitor discharge component 208 is connected across the capacitor for intermittently discharging the signal accumulated in the capacitor. The discharge is typically accomplished between depositions of medicament to remove the residual charge from a previous deposit. The high impedance amplifier 210 is connected to the capacitor and output port of the filter such that the signal accumulated on the capacitor is amplified to a useful level.

The output of the integrator 202, the integrated signal, is applied to one port of the comparator 204. The magnitude of the integrated signal is directly proportional to the amount of charge accumulated upon the dielectric substrate 110, e.g., as the charge accumulates more ion current flows and the magnitude of the integrated signal increases. A second port of the comparator is connected to a threshold voltage source 212. The source 212 provides a threshold signal to which the comparator compares the integrated signal. When the integrated signal exceeds the threshold level, the charge control circuit 108 deactivates the AC signal source driving the print head. Conversely, as long as the integrated signal magnitude is less than the threshold level, the AC signal source remains activated and the charge accumulates upon the substrate.

The charge accumulation on the substrate is proportional to the size of the region that is charged by the print head. In accordance with ionographic printing terminology, this region, which is typically circular, is commonly referred to as a "dot size". The dot size is related to the accumulated charge by the following equation:

$$\text{dot size} = \text{dot size}_0\sqrt{\frac{q}{q_0}} \tag{1}$$

where:

dot size is a diameter of a circular region in which charge is accumulated on the substrate;

q is the accumulated charge quantity to produce a particular dot size; and $q_0$ is a reference charge quantity to generate reference dot size (dot $\text{size}_0$). The reference charge quantity and dot size are empirically predetermined for a particular dielectric material and dielectric material thickness. Once the reference charge quantity and reference dot size are determined, equation (1) is used to compute the dot size for any given charge quantity. Thus, the threshold level in the charge control circuit is correlated to one or more dot sizes. As such, the threshold level is set to deactivate the AC signal source when a particular level is exceeded such that a particular dot size is generated for that threshold level. Further, a series of selectable threshold levels can be provided such that a user can select a particular dot size to be generated for a particular medicament being deposited at that time. Thus, this form of medicament deposition is very flexible and very useful in controlling the medicament dose that is deposited upon the substrate.

Once the substrate is charged, the medicament must then be deposited upon the charged region of the substrate. In this regard, a medicament cloud is provided proximate the charged region of the substrate. The medicament particles in the cloud, being positively charged (if the substrate is negatively charged), are attracted to the negatively charged region of the substrate and electrostatically deposit themselves on the charged region of the substrate. Of course, the medicament cloud is negatively charged, if the substrate has been positively charged.

Figure 3:
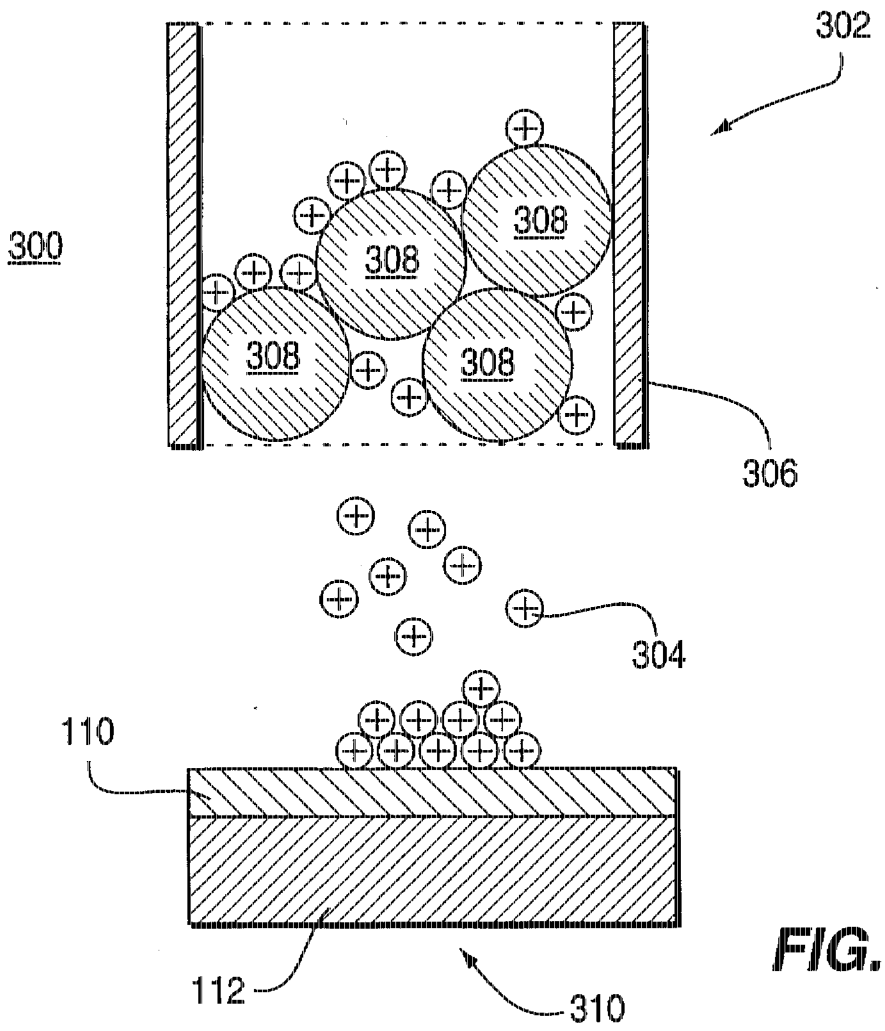
FIG. 3 depicts a cross-sectional view of a triboelectric charging container for charging a medicament powder and a cross-sectional view of a portion of a substrate upon which the charged medicament powder is deposited.

FIG. 3 depicts a cross-sectional view of apparatus 300 for charging the medicament particles and depositing the charged particles upon the substrate. Specifically, the invention uses a triboelectric charging technique to charge the medicament. Such a technique effectively charges the medicament particles such that, when dispersed into a cloud, the charge-to-mass ratio on each particle is substantially uniform throughout the cloud. Consequently, given a repeatable quantity of charge on the substrate and such a repeatable charge-to-mass ratio on the medicament particles, a repeatable amount of medicament is attracted to and remains electrostatically adhered to the substrate. The electrostatic attraction or adhesion between the medicament powder and the substrate remains, without significant degradation, for months.

Medicament charging and deposition apparatus 300 contains a triboelectric charger 302, medicament powder 304, and the charged substrate 110 supported upon a conductive plate 112. The substrate has a charged region 310 (dot size) that has been locally charged as previously discussed with an ion or electron emitter. The triboelectric charger 302 is a cylindrical, glass container 306 containing a plurality of glass or plastic beads 308 (e.g., four beads) and the powdered medicament 304. Illustratively, the beads have a diameter of between 50 and 200 microns and are fabricated of one of the following materials Teflon, kynar, polypropylene, maroon polypropylene, flouro-treated glass, glass, amino-treated glass, polystyrene, white miliken and the like. The container 306 has a mesh, typically wire, at each end. The mesh defines openings (e.g., 400 mesh screen) that permit the medicament powder to ingress and egress from the container. In use, the medicament is added to the container, the mesh ends of the container are closed off and the beads and medicament mixture is shaken for 1 to 10 minutes. During the shaking process, a charge accumulates on the particles of the powder. Once charged, a gas (e.g., air or nitrogen) is blown through the container and medicament particles form a cloud proximate the surface of the substrate.

The amount and polarity of the charge on the medicament particles depends upon the fabrication material of the beads. By measuring the charge-to-mass ratio of the powder using a faraday cage, the inventors have found that by selecting a particular bead material the charge characteristics are controllable. For example, charging a mometasone furoate (MF) powder in a glass container using four beads having 50 to 100 micron diameters at 70 degrees Fahrenheit and 45% relative humidity, resulted in the charge-to-mass ratios for various bead materials shown in Table 1.

TABLE 1

| Bead Material | Charge Polarity | Ratio (μC/gm) |
|---|---|---|
| Teflon | positive | 35 |
| Kynar | positive | 30 |
| Polypropylene | positive | 6.5 |
| Maroon polypropylene | positive | 10 |
| Flouro-treated glass | positive | 17.8 |
| Glass | negative | 6.5 |
| Amino-treated glass | negative | 39.8 |
| Polystyrene | negative | 42.7 |
| White miliken | negative | 7.7 |

By appropriate selection of the bead material, the charge-to-mass ratio can be varied form 6.5 to 43 μC/gm and the charge is either positive or negative. When accurately depositing a medicament, a low microgram quantity of medicament (e.g., 2–10 μg) requires a relatively high charge-to-mass ratio and a high microgram quantity of medicament (e.g., 20–40 μg) requires a relatively low charge-to-mass ratio. Using the triboelectric medicament charging technique in combination with the electrostatic substrate charging technique, a 10 to 200 μg quantity of medicament can be accurately positioned on the substrate. Furthermore, the adherence of such quantities of medicament to a 2 mil thick, polypropylene substrate is strong enough to withstand a 48 inch drop test without dislodging any of the medicament from the substrate. This substantial adhesion property is attributed to electrostatic and short range van der Waals forces.

Once deposited, the substrate is positioned near a vacuum system to remove any medicament powder that has not electrostatically adhered to the substrate. In a practical medicament dosing substrate, a plurality of locations on the substrate are charged and then medicament is deposited at each of the charged locations. Thereafter, the vacuum system removes any excess medicament powder that is not adhered to the charged locations.

Alternatively, since the unadhered medicament powder (background powder) is typically a relatively small quantity of medicament, it can simply be left on the substrate. If this approach is used, the amount of charge deposited should be slightly reduced such that slightly less medicament is adhered to the substrate.

Figure 4:
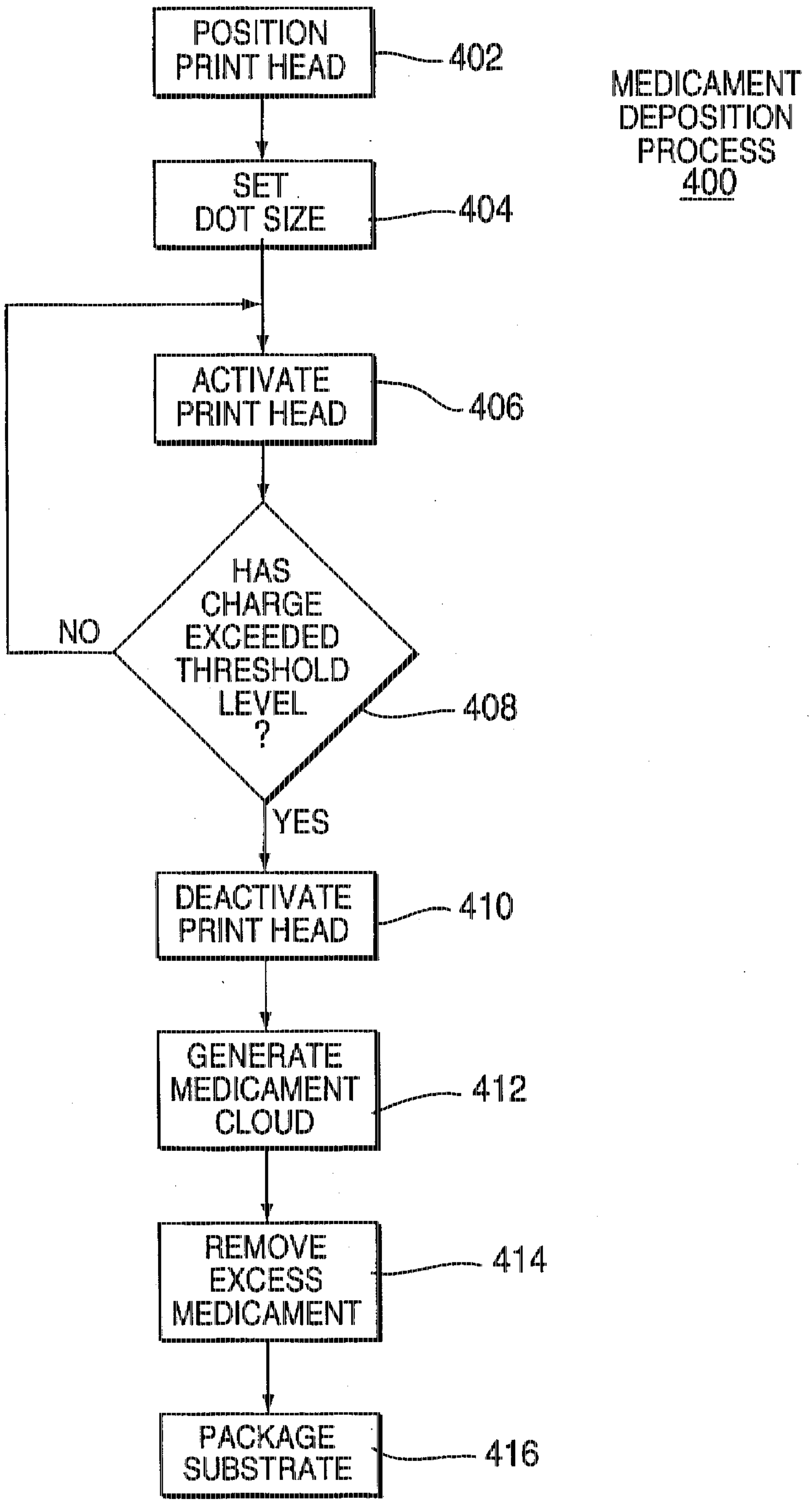
FIG. 4 depicts a flow chart of the electrostatic deposition process.

FIG. 4 depicts a flow chart summarizing the process used to electrostatically deposit medicament onto a substrate. Deposition process 400 begins, at step 402, by positioning the print head over a particular location on a substrate. At step 404, a user selects the dot size to be "printed" by selecting a threshold level for the charge control circuit. The process, at step 406, activates the print head and begins bombarding the selected location on the substrate with ions. The process queries, at step 408, whether the threshold level has been exceeded by the accumulated charge on the substrate. If the query is negatively answered, the print head remains active and charge continues to accumulate on the substrate. When the query of step 408 is affirmatively answered, the process, at step 410, deactivates the print head. At this point in the process a "dot" of charge having a diameter commensurate with the dot size selected in step 404 has been deposited at the selected location upon the substrate. Of course, rather than a single dot, the print head could be moved relative to the substrate to form a charged pattern on the substrate, e.g., a line, a square, a circle, and the like.

Once the charge is deposited, the triboelectric charging apparatus produces a charged cloud of medicament proximate the surface of the substrate. Specifically, the process, at step 412, produces this cloud of medicament as described above with respect to FIG. 3. A predefined dose of medicament adheres to the charged dot on the substrate. As discussed above, the quantity of medicament in the dose depends on the charge accumulated on the substrate and the charge-to-mass ratio of charge on the medicament powder. At step 414, excess medicament is removed, for example, by a vacuum system. The excess medicament can be recycled for deposition at another time. Lastly, at step 416, the substrate and its medicament are packaged.

The forgoing electrostatic deposition process can further be used in what is known as a reverse development process. In general, the reverse development process scans the print head over the substrate (or the substrate can be moved past the print head) to deposit charge at all locations on the substrate except those locations where the medicament is to be deposited.

Figure 5:
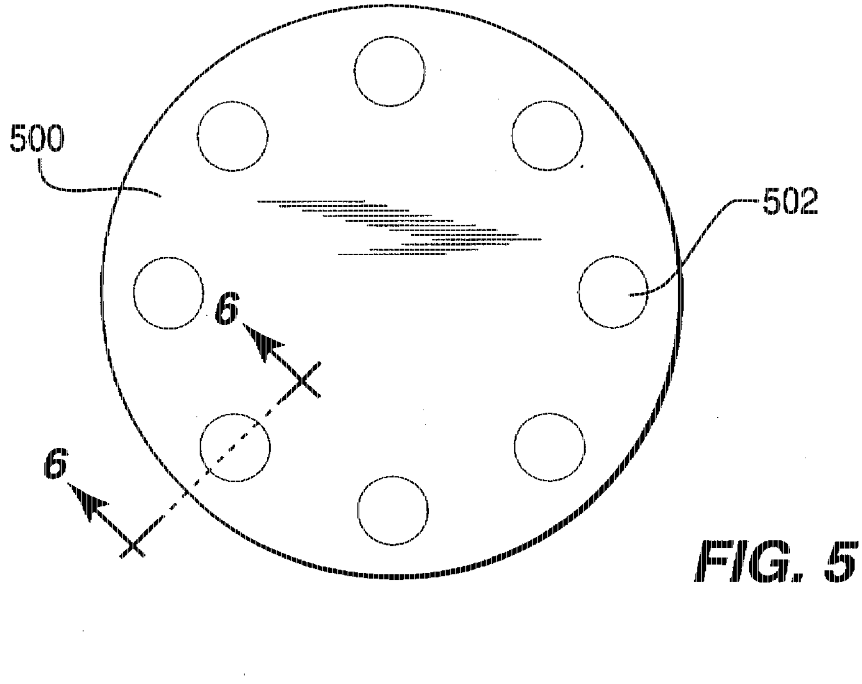
FIG. 5 depicts a top, perspective view of a substrate that has been charged using a reverse development charging technique.

FIG. 5 depicts a top view of a disk-shaped substrate 500 having a plurality of medicament deposition locations 502. The gray area on the substrate indicates the area in which a charge is deposited by the print head. Conversely, locations 502 contain no charge.

Figure 6:
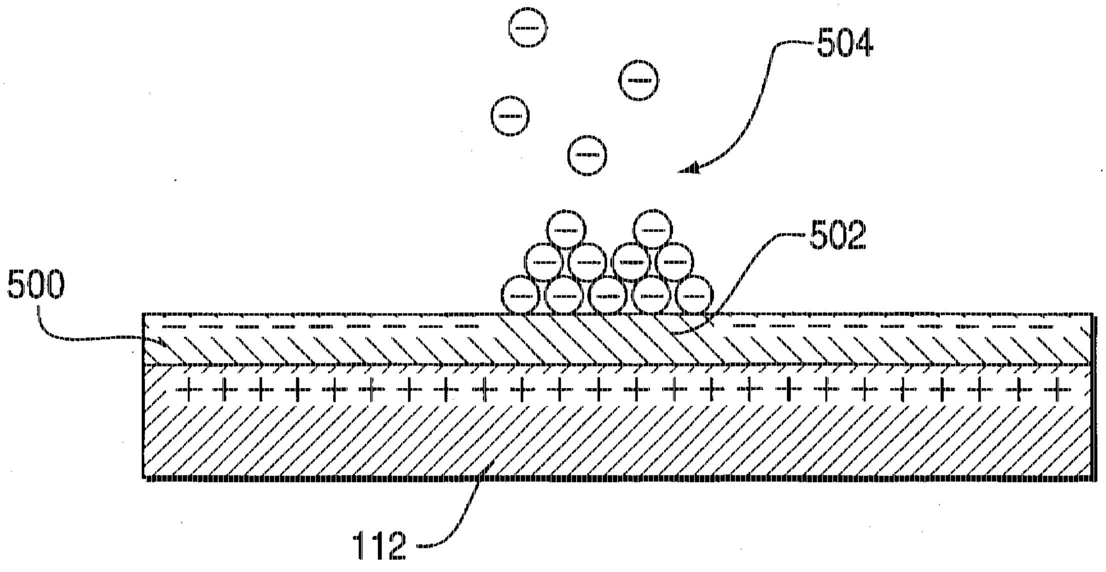
FIG. 6 depicts a cross-sectional view of the substrate along line 6—6 in FIG. 5.

As depicted in the cross-sectional view of a portion of the substrate 502 in FIG. 6 taken along line 6—6 in FIG. 5, if the substrate charge is negative, the conductive plate 112, positioned beneath the substrate 500, is positively charged across its entire surface that contacts the substrate 500. The medicament 504 is negatively charged using, for example, the triboelectric charging technique discussed above. The negatively charged medicament electrostatically adheres to the substrate 500 in uncharged region 502, i.e., the negatively charged medicament is attracted to the positively charged plate. Additionally, the negatively charged medicament is repelled from the negatively charged surface of the substrate. Consequently, medicament only accumulates and adheres to the uncharged substrate regions 502. To release the medicament, the plate is discharged, typically by grounding. Such discharge removes the electrostatic force maintaining the medicament upon the substrate. Consequently, once the charge is removed, the medicament can be easily removed from the substrate using a venturi or direct inhalation device (as discussed below with respect to FIG. 7). To facilitate release of single medicament doses, the conductive plate is segmented (or patterned) and each plate segment is located below each region 502. As such, each plate segment can be individually charged and discharged. Thus, each dose of medicament can be individually released from the substrate.

A variation of the reverse deposition technique forms another embodiment of the invention. This alternative involves utilization of a photoconductive disk as a substrate upon which the medicament is deposited. Illustratively, the photoconductive disk is a polymeric substrate coated with a photoconductive zinc oxide in a resin binder. A print head charging technique is used to negatively charge the entire surface of the disk. Thereafter, a light mask having a plurality of apertures therethrough is positioned over the substrate and the mask is bathed in light. Consequently, the substrate surface exposed to the light via the apertures in the mask is discharged of the negative charge. After the mask is removed, the disk is charged in a manner that resembles the substrate depicted in FIG. 5, i.e., charge is deposited in all locations except locations where the medicament is to be deposited. The negatively charged medicament powder is deposited in the uncharged regions in the same manner as described above with respect to FIG. 6. The medicament powder is released from the substrate by exposing a selected dose of the medicament and an area surrounding the selected dose to light. Such light exposure discharges the electrostatic force and releases the medicament powder from the substrate. Thereafter, the medicament can be inhaled using a venturi or direct inhalation device as discussed below.

Figure 7:
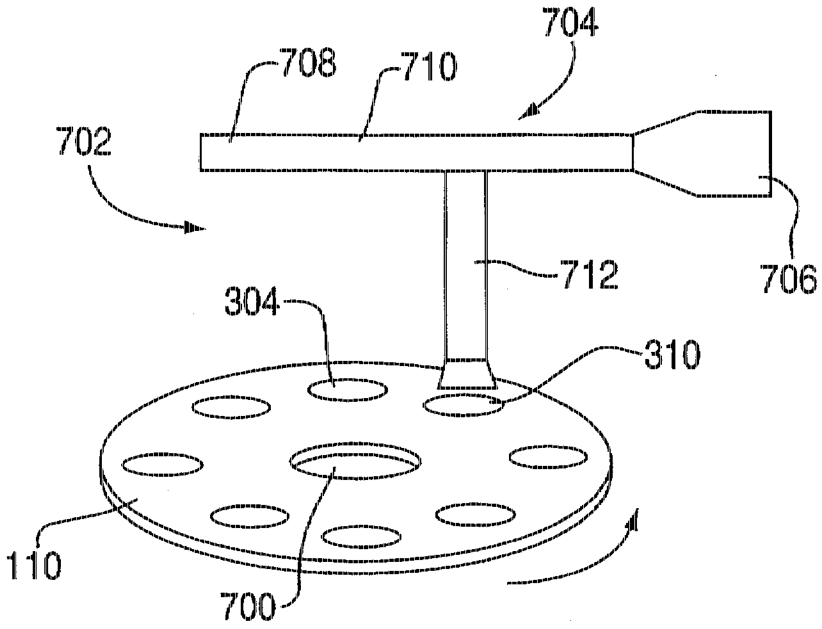
FIG. 7 depicts a perspective view of an illustrative substrate having had dry powder deposited at a plurality of select locations thereupon and an illustrative inhalation device for releasing the medicament from the substrate.

FIG. 7 depicts an illustrative substrate having medicament deposited at predefined locations using one of the electrostatic deposition processes discussed above with respect to FIGS. 4, 5 and 6. The substrate 110 of FIG. 7 is a disk shaped dielectric that contains a plurality of locations 310 to which medicament 304 electrostatically adheres. A central hole 700 is provided to permit the substrate to be supported within an inhaler device 702. This exemplary inhaler device 702 uses the venturi principle to extract the medicament from the substrate. The inhaler contains a housing (not shown) that surrounds the substrate and supports the venturi inhaler apparatus 704 and the substrate 110. The venturi inhaler apparatus contains a main air flow tube 710 having a mouthpiece 706 and an inlet end 708. Approximately midway along the main air flow tube is a medicament tube 712 that orthogonally intersects and is coupled to the main tube 710. The medicament tube 712 is positioned over a medicament location 310 by rotating the substrate 110 relative to the venturi apparatus 704. A patient then inhales through the mouthpiece 706 drawing air through inlet end 708 of the tube 710. As air flows toward the mouthpiece 706, the venturi effect also draws air through tube 712. As air is drawn through tube 712, the medicament is dislodged from the substrate and carried to the patient's mouth. When another dose is required, the patient rotates the substrate to the next dose on the disk and again inhales the medicament.

To permit a substantial air flow along tube 712, the substrate, rather than being a solid layer of dielectric material, may be a woven or perforated substrate. Such substrates include a metallic mesh coated with a dielectric material such as Teflon, a textile such as silk, a perforated solid dielectric layer, and the like. The perforations are small relative to the particle size of the medicament, but large enough to allow air to pass therethrough. As such, when a patient inhales on the mouthpiece, air passes through the substrate 110 and along tube 712. The air flow carries the medicament to the patient.

Additionally, when using a perforated substrate, a venturi effect inhaler is not necessary and can be substituted with a simple inhalation tube. Such an inhaler device contains a flexible inhalation tube supported by a housing and having an inlet end located proximate medicament location. In essence, this is the venturi inhalation apparatus without a main air How tube 710, where the patient merely inhales on the medicament tube 712. In use, an inlet end of an inhalation tube is positioned proximate a medicament location by rotating the substrate within the housing. Thereafter, the patient simply inhales the medicament directly from the perforated substrate, through the inhalation tube and into their lungs. The perforated substrate significantly increases the velocity of the air How that removes the medicament from the substrate over that of a venturi effect device used in combination with a solid substrate.

Those skilled in the art will realize that many other forms of inhaler devices can be employed to dislodge the medicament from the substrate, including those that employ compressed gas or air to remove the medicament and generate an inhalable cloud. Any of these inhaler devices are to be considered within the scope of the invention.

In each of the foregoing embodiments of the invention, the substrate may be fabricated of Teflon, polystyrene, polypropylene and the like. In general, any material that will retain an electrostatic charge is sufficient. The substrate, may or may not, be perforated to enable inhalation of air through the substrate as discussed above. In a further example of the invention being used to produce oral medication, including capsules, tablets, vaginal and rectal suppositories and the like, the electrostatic deposition technique of the invention is used to electrostatically deposit specific quantities of powdered medicament upon an edible substrate such as cellulose. The substrate is then encapsulated in a inert material to form a capsule, tablet, or suppository. Substrates useful for this application are typically polymeric substances that preferably self-destruct or are degraded in body fluids and/or enzymes. However, the substrate can be a non-destructible substance that is readily eliminated from the body once the medicament has been released into the body from the substrate.

Although various embodiments which incorporate the teachings of the present invention have been shown and described in detail herein, those skilled in the art can readily devise many other varied embodiments that still incorporate these teachings.

What is claimed is:

1. Apparatus for electrostatically depositing a medicament powder upon selected regions of a substrate, said apparatus comprising:

an ion emitter;

a substrate spaced apart from said emitter and located upon a conductive plate, where ions emitted from the ion emitter, upon impact with a predefined region of a surface of said substrate, locally charge said substrate at said predefined region; and a powder cloud generator, wherein the powder cloud generator generates a cloud of medicament powder proximate said predefined region on said substrate;

wherein a plurality of powder particles within said cloud adhere to said predefined region of said substrate.

2. The apparatus of claim 1 wherein said substrate is perforated.

3. The apparatus of claim 1 wherein the substrate is a woven mesh coated with a dielectric material.

4. The apparatus of claim 1 further comprising:

a charge accumulation controller, coupled to said emitter and said conductive plate, for comparing the charge accumulated upon the substrate to a threshold charge value and for deactivating said emitter when said comparison generates a deactivation signal.

5. The apparatus of claim 4 wherein said charge accumulation controller comprises an integrator for integrating the charge accumulated upon said substrate and for generating a voltage value indicative of the accumulated charge on the substrate.

6. The apparatus of claim 4 wherein said charge accumulation controller controls the size of the charged region on the substrate by measuring the accumulated charge on the substrate relative to a reference charge value that corresponds to a reference size of he charged region.

7. The apparatus of claim 5 wherein said charge accumulation controller further comprises a low pass filter connected between said conductive plate and said integrator.

8. The apparatus of claim 1 wherein said powder cloud forming means is a triboelectric charging apparatus.

9. The apparatus of claim 8 wherein said triboelectric apparatus further comprises a plurality of beads that are fabricated of a selected material that generates substantially the same charge-to-mass ratio for each particle of medicament powder within said charged cloud of medicament powder.

10. The apparatus of claim 1 wherein said medicament powder is deposited at a plurality of predefined regions upon said substrate.

11. The apparatus of claim 1 further comprising means for releasing said medicament from said substrate.

12. The apparatus of claim 11 wherein said releasing means is a venturi effect inhaler.

13. The apparatus of claim 11 wherein said releasing means is a inhalation tube for inhaling said medicament directly from the substrate.

14. The apparatus of claim 13 wherein said substrate is perforated.

15. The apparatus of claim 13 wherein the substrate is a woven mesh coated with a dielectric material.

16. Apparatus for electrostatically depositing a medicament powder upon selected regions of a substrate, said apparatus comprising:

an ion emitter;

a substrate spaced apart from said emitter and located upon a conductive plate, where ions emitted from the ion emitter, upon impact with a predefined region of a surface of said substrate, locally charge said substrate at said predefined region; and a powder cloud generator, wherein the powder cloud generator generates a cloud of medicament powder proximate said predefined region on said substrate;

wherein a plurality of powder particles within said cloud adhere to any region other than said predefined region of said substrate.

17. The apparatus of claim 16 further comprising:

a charge accumulation controller, coupled to said emitter and said conductive plate, for comparing the charge accumulated upon the substrate to a threshold charge value and for deactivating said emitter when said comparison generates a deactivation signal.

18. The apparatus of claim 16 wherein said powder cloud forming means is a triboelectric charging apparatus.

19. The apparatus of claim 18 wherein said triboelectric apparatus generates substantially the same charge-to-mass ratio for each particle of medicament powder within said charged cloud of medicament powder.

20. The apparatus of claim 16 wherein said medicament powder is deposited upon said substrate at a plurality of regions other than said predefined region.

21. The apparatus of claim 16 further comprising means for releasing said medicament from said substrate.

22. The apparatus of claim 21 wherein said releasing means is a venturi effect inhaler.

23. The apparatus of claim 22 wherein said releasing means is a inhalation tube for inhaling said medicament directly from the substrate.

24. The apparatus of claim 23 wherein said substrate is perforated.

25. The apparatus of claim 23 wherein the substrate is a woven mesh coated with a dielectric material.

26. Apparatus for electrostatically depositing a medicament powder upon selected region of a substrate, said apparatus comprising:

an ion emitter;

a photoconductive substrate spaced apart from said emitter and located upon a conductive plate, where ions generated by the ion emitter, upon impact with a surface of said photoconductive substrate, charge the surface of said substrate;

a light mask, applied to said charged substrate surface, for selectively applying light to cause discharging of any region of said photoconductive substrate not covered by said light mask; and a powder cloud generator, wherein the powder cloud generator generates a cloud of medicament powder proximate said predefined region on said substrate;

wherein a plurality of powder particles within said cloud adhere to any region other than a charged region of said substrate.

27. The apparatus of claim 26 wherein said powder cloud forming means is a triboelectric charging apparatus.

28. The apparatus of claim 27 wherein said triboelectric apparatus generates substantially the same charge-to-mass ratio for each particle of medicament powder within said charged cloud of medicament powder.

29. The apparatus of claim 26 wherein said medicament powder is deposited upon said photoconductive substrate at a plurality of uncharged regions.

30. The apparatus of claim 26 further comprising means for releasing said medicament from said substrate.

31. The apparatus of claim 30 wherein said releasing means is a venturi effect inhaler.

32. The apparatus of claim 31 wherein said releasing means is a inhalation tube for inhaling said medicament directly from the substrate.

33. The apparatus of claim 31 wherein said substrate is perforated.

34. The apparatus of claim 31 wherein the substrate is a woven mesh coated with a dielectric material.

* * * * *